United States Patent [19]

Schulze et al.

[11] Patent Number: 5,797,941
[45] Date of Patent: Aug. 25, 1998

[54] SURGICAL INSTRUMENT WITH EXPANDABLE CUTTING ELEMENT

[75] Inventors: Dale Schulze, Lebanon; William D. Fox, New Richmond, both of Ohio

[73] Assignee: Ethicon Endo-Surgery, Inc., Cincinnati, Ohio

[21] Appl. No.: 804,845

[22] Filed: Feb. 24, 1997

Related U.S. Application Data

[63] Continuation of Ser. No. 395,732, Mar. 1, 1995, abandoned, which is a continuation-in-part of Ser. No. 382,463, Feb. 3, 1995, abandoned.

[51] Int. Cl.⁶ ............................. A61B 17/32; A61B 17/39
[52] U.S. Cl. ........................................... 606/171; 606/51
[58] Field of Search .................. 606/45, 46, 49–52, 606/170, 171

[56] References Cited

U.S. PATENT DOCUMENTS

| | | | |
|---|---|---|---|
| 1,798,902 | 3/1931 | Raney . | |
| 1,881,250 | 10/1932 | Tomlinson . | |
| 2,031,682 | 2/1936 | Wappler et al. | 174/89 |
| 2,068,721 | 1/1937 | Wappler et al. | 128/303.15 |
| 4,375,218 | 3/1983 | DiGeronimo | 128/303.17 |
| 4,655,216 | 4/1987 | Tischer | 128/303.17 |
| 4,671,274 | 6/1987 | Sorochenko | 128/303.14 |
| 5,057,107 | 10/1991 | Parins et al. | 606/48 |
| 5,123,904 | 6/1992 | Shimomura | 606/170 |
| 5,151,102 | 9/1992 | Kamiyama et al. | 606/51 |
| 5,190,541 | 3/1993 | Abele et al. | 606/46 |
| 5,201,900 | 4/1993 | Nardella | 606/157 |
| 5,207,691 | 5/1993 | Nardella | 606/142 |
| 5,360,428 | 11/1994 | Hutchinson, Jr. | 606/45 |
| 5,389,098 | 2/1995 | Tsuruta et al. | 606/41 |
| 5,403,312 | 4/1995 | Yates et al. | 606/50 |
| 5,417,687 | 5/1995 | Nardella et al. | 606/32 |
| 5,445,638 | 8/1995 | Rydell et al. | 606/51 |
| 5,458,598 | 10/1995 | Feinberg | 606/52 |
| 5,531,744 | 7/1996 | Nardella et al. | 606/45 |

FOREIGN PATENT DOCUMENTS

| | | |
|---|---|---|
| 0369324 | 5/1990 | European Pat. Off. ........... 606/170 |
| 0 517 244 A1 | 12/1992 | European Pat. Off. . |
| 0 518 230 A1 | 12/1992 | European Pat. Off. . |
| 0724863A2 | 8/1996 | European Pat. Off. . |
| 4303882A1 | 8/1994 | Germany . |
| WO 93/08754 | 5/1993 | WIPO . |
| WO 94/24949 | 11/1994 | WIPO . |
| WO 94/24951 | 11/1994 | WIPO . |

OTHER PUBLICATIONS

Two New Laparoscopic Instruments: Bipolar Sterilizing Forceps and Uterine Manipulator; Corson, Stephen L., Medical Instrumentation, vol. 11, No. 1, (Jan.–Feb. 1977).

*Primary Examiner*—Lee S. Cohen
*Attorney, Agent, or Firm*—Bernard Shay

[57] ABSTRACT

A surgical instrument is provided for clamping and cutting during surgical procedures, particularly for use with tissues of varying thicknesses. The instrument in a preferred embodiment compresses tissue between electrodes associated with jaws of the clamping device and applies electrosurgical energy to the tissue. The invention provides an expandable cutting element which is adapted to compensate for various thicknesses in tissue and contractible by providing a knife which can be contained within the jaws and expand as needed for thicker tissues. The cutting element is preferably actuated as or after the electrosurgical energy has been applied, to cut tissue engaged and treated by the jaw members.

4 Claims, 6 Drawing Sheets

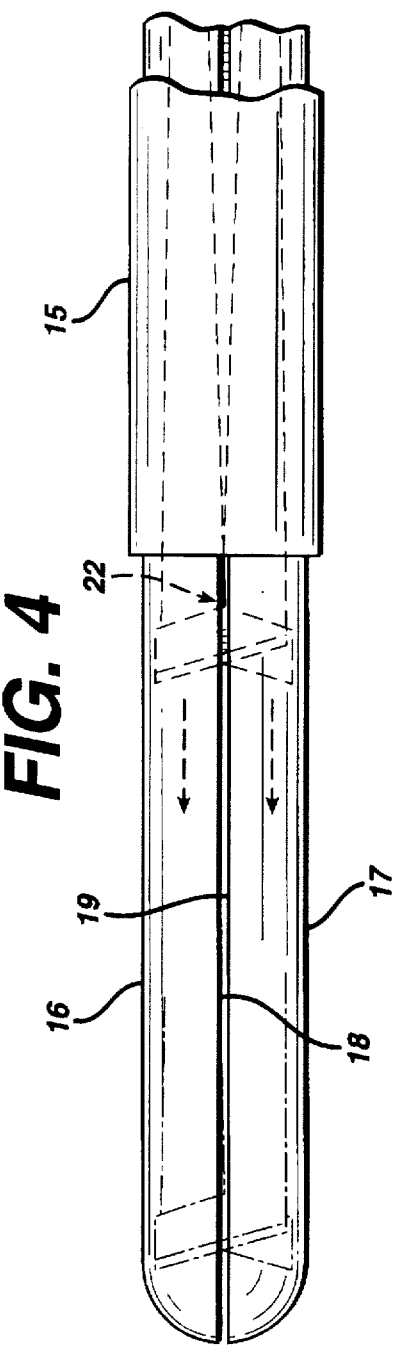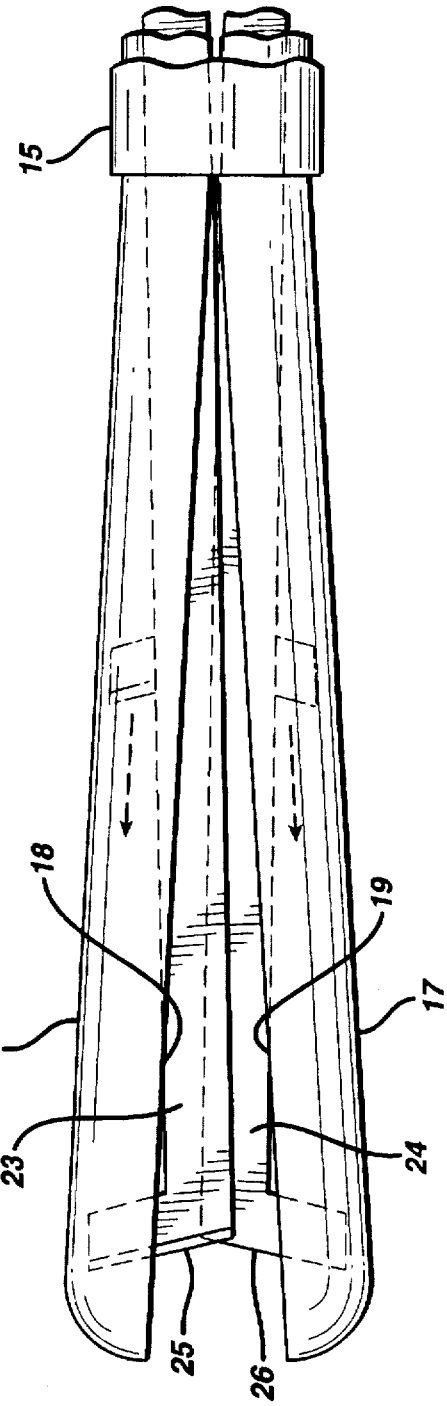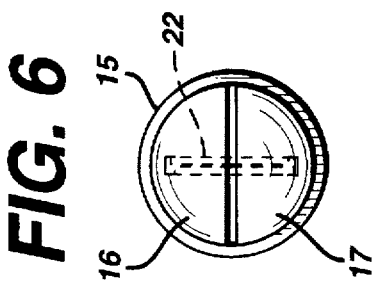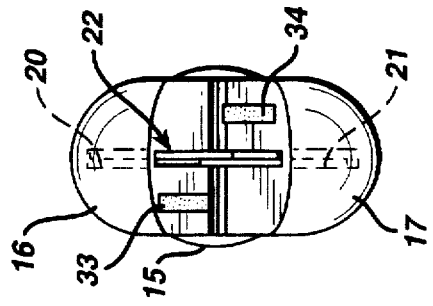

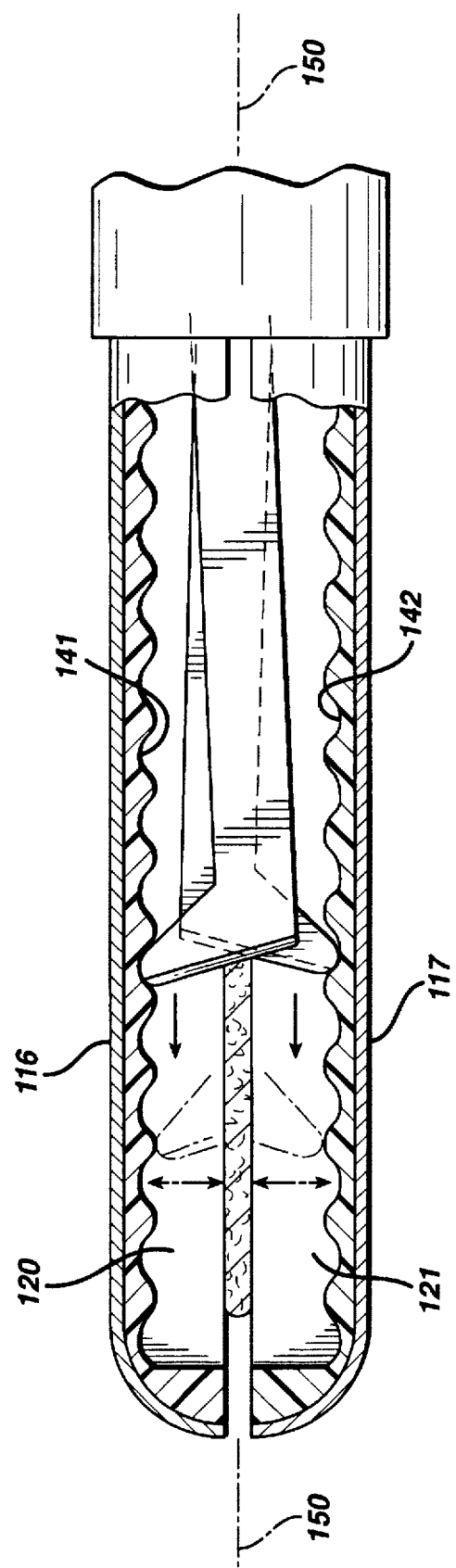

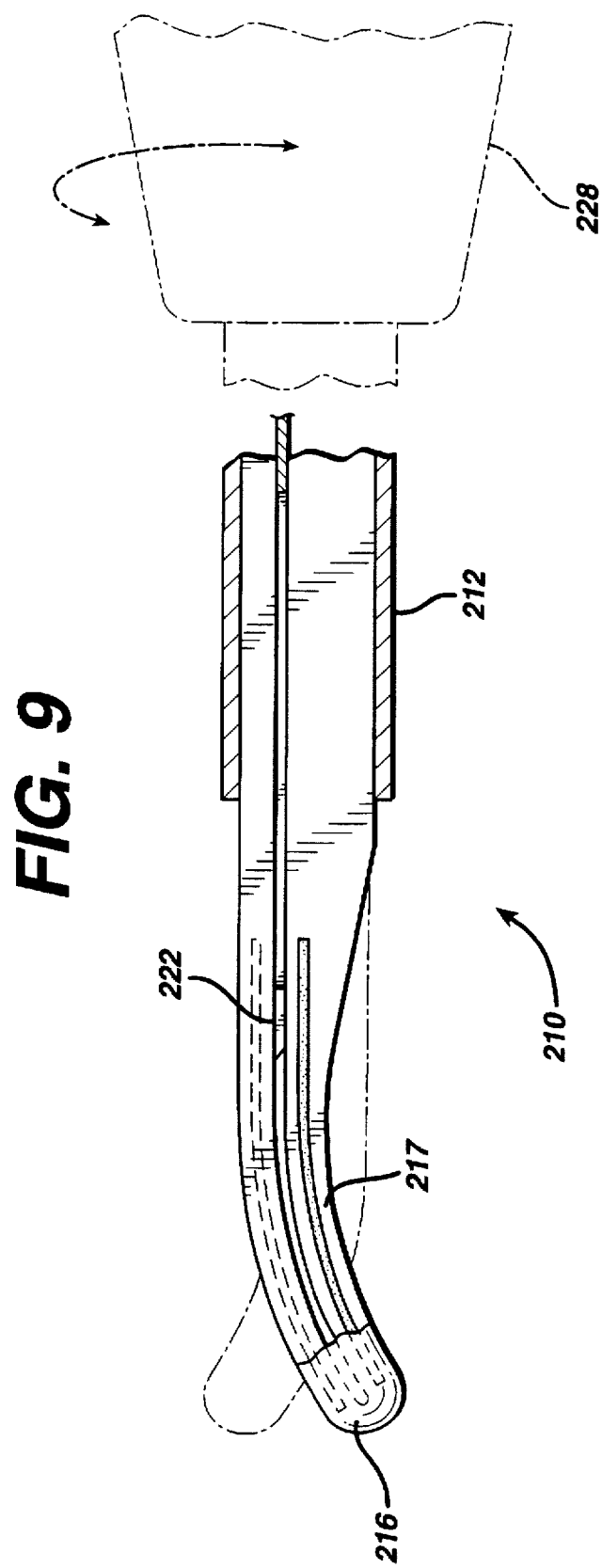

SURGICAL INSTRUMENT WITH EXPANDABLE CUTTING ELEMENT

This is a continuation, of application Ser. No. 08/395,732, filed Mar. 1, 1995, now abandoned, which is a Continuation-In Part of U.S. application Ser. No. 08/382,463 filed on Feb. 3, 1995, now abandoned incorporated herein by reference.

FIELD OF THE INVENTION

This invention relates to a surgical instrument for cutting tissue in the performance of surgical procedures, especially an electrosurgical instrument for electrosurgically treating tissue.

BACKGROUND OF THE INVENTION

Simple clamping and cutting devices are known in the art and are used in surgical procedures. For example, linear cutting and stapling instruments provides two jaw members and an end effector for grasping and holding tissue as staples are applied and a knife is passed through the tissue. In such an instrument the jaws typically close to a predetermined gap spaced apart by a gap pin. The knife advances through a knife channel formed in the jaws to cut the tissue as it is being stapled.

Electrocautery devices have been used for effecting improved hemostasis by heating tissue and blood vessels to cause coagulation or cauterization. Monopolar devices utilize one electrode associated with cutting or cauterizing instrument and a remote return electrode, usually adhered externally to the patient. More recently, bipolar instruments have been used because the cauterizing current is generally limited to tissue between two electrodes of a tissue treating portion of an instrument.

Bipolar forceps have been used for cutting and/or coagulation in various procedures. Generally bipolar forceps grasp tissue between two poles and apply an electrical current through the grasped tissue.

U.S. Pat. No. 4,655,216 discloses an electrosurgical grasping device including a biopsy tissue cutting device arranged to provide a pivoting scissors-like cutting action to obtain a biopsy sample. The grasping jaws provide electrocautery energy to the grasped tissue.

U.S. application Ser. No. 08/95,797, now U.S. Pat. No. 5,403,312, incorporated herein by reference, describes an electrosurgical device having two jaw members which close together to compress and apply electrosurgical energy to tissue engaged therebetween. A cutting element is described which is arranged to move through the jaw members to sever tissue engaged therebetween.

One disadvantage of the known devices is that the devices are not adapted to be used in a forceps-like tissue coagulating device in which relatively varying sizes of tissue (i.e. relative to the size of the end effector jaw members) can be treated (e.g., electrosurgically) and cut. A second disadvantage is that the cutting means at the known devices extend beyond the surface(s) of the forceps jaw members, thus allowing the possibility of inadvertently cutting tissue outside the grasp of the jaw members.

Thus, a need exists for a clamping and cutting device which is capable of adapting to varying thicknesses of tissue to provide improved cutting of tissue, and which also has a cutting means that is not exposed to adjacent tissues not intended to be cut.

SUMMARY OF THE INVENTION

Accordingly, the present invention provides a clamping device for grasping, clamping or approximating tissue. The end effector, i.e. tissue clamping, grasping or approximating portion of the instrument, includes an expandable knife, or cutting element, adaptive in size to expand or contract in response to the amount of tissue grasped or clamped by jaw members of the device.

In one embodiment, the cutting element comprises overlapping blade members which form a single cutting blade. The blade members are biased away from each other into grooves formed in jaw members so that when the jaw members are opened, the blade members will expand away from each other, decreasing the area of overlap and increasing the size of the cutting blade. When the jaws are closed together, the overlap area increases and the cutting blade correspondingly decreases in size to fit the gap between the jaws members at the location of the cutting blade. This device also provides a cutting element adaptive to the varying gap between the jaw members along the length of the jaw members.

In a preferred embodiment, an electrosurgical tissue treating device is provided in which electrosurgical energy is delivered to tissue engaged by the end effector jaw members. An expandable knife is provided for cutting the tissue engaged by the jaw members, preferably after electrosurgical energy has been delivered to the tissue.

These and other objects of the invention will be better understood from the following attached detailed Description of the Drawings, when taken in conjunction with the Detailed Description of the Invention.

DESCRIPTION OF THE DRAWINGS

FIG. 4 illustrates a side-elevational view of the distal portion of the device of FIG. 1 in use with thin tissue;

FIG. 5 illustrates a side-elevational view of the distal portion of the device of FIG. 1 in use with thick tissue;

FIG. 6 illustrates a front end view of FIG. 4;

FIG. 7 illustrates a front end view of FIG. 5;

FIG. 8 illustrates a side cross-sectional view of the distal of an alternative embodiment of the present invention; and FIG. 9 illustrates a top cross-sectional view of the distal portion of an alternative embodiment of the present invention.

DETAILED DESCRIPTION OF THE DRAWINGS

Figure 1:
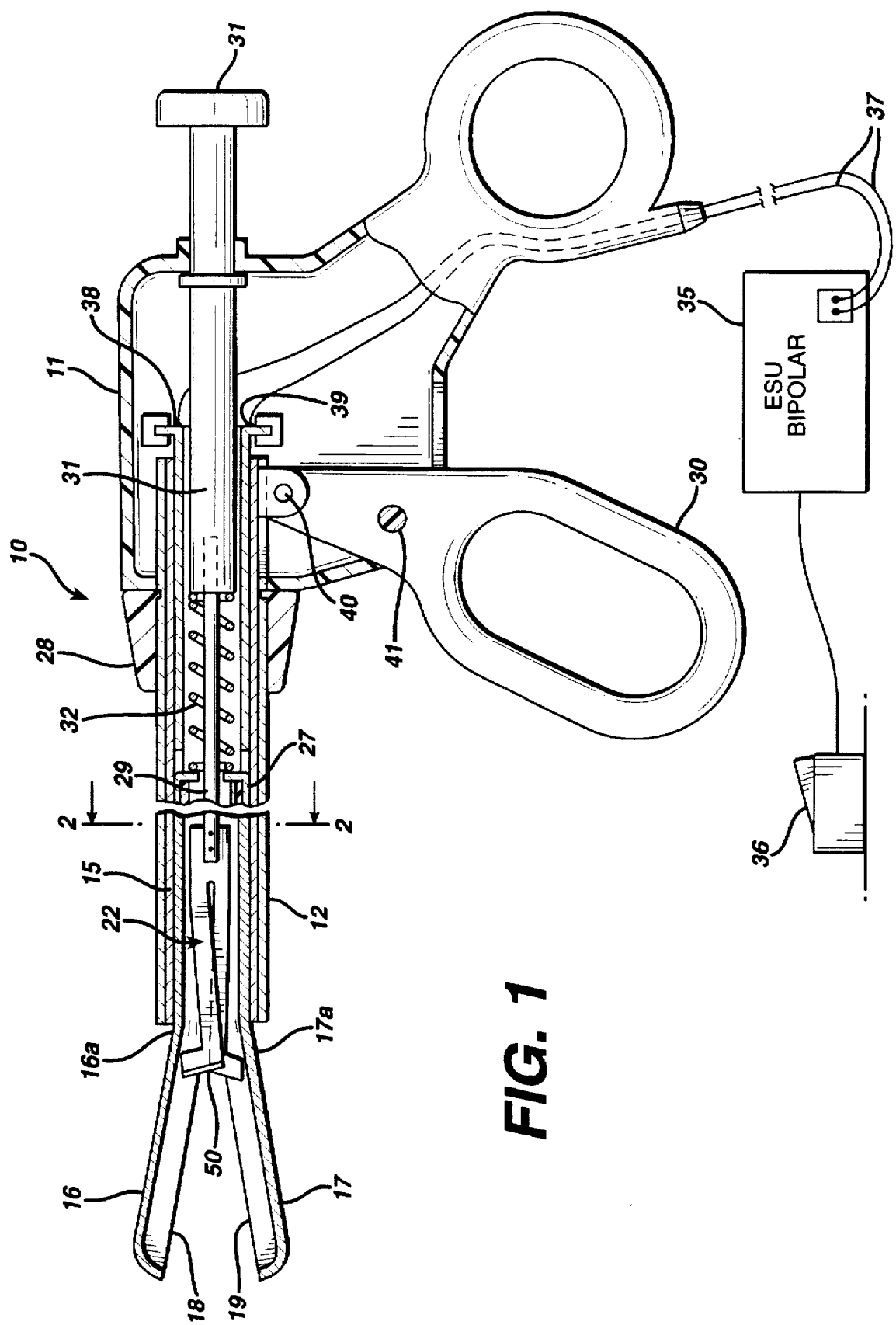
FIG. 1 is a side elevational cross-sectional of the clamping, cutting and coagulating device of a preferred embodiment of the present invention.
Figure 2:
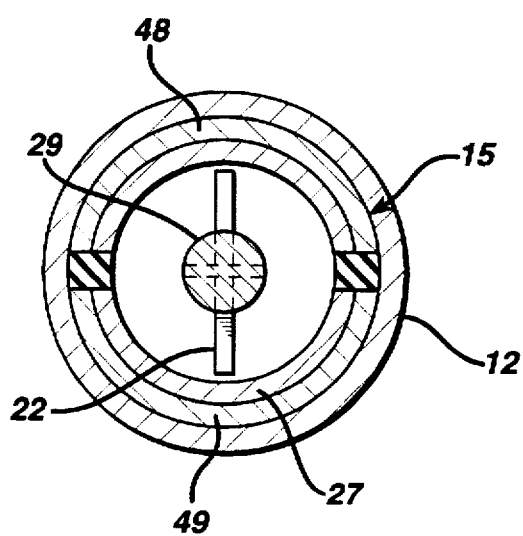
FIG. 2 is a front cross-sectional view of the device of FIG. 1 along the lines 2—2.
Figure 3:
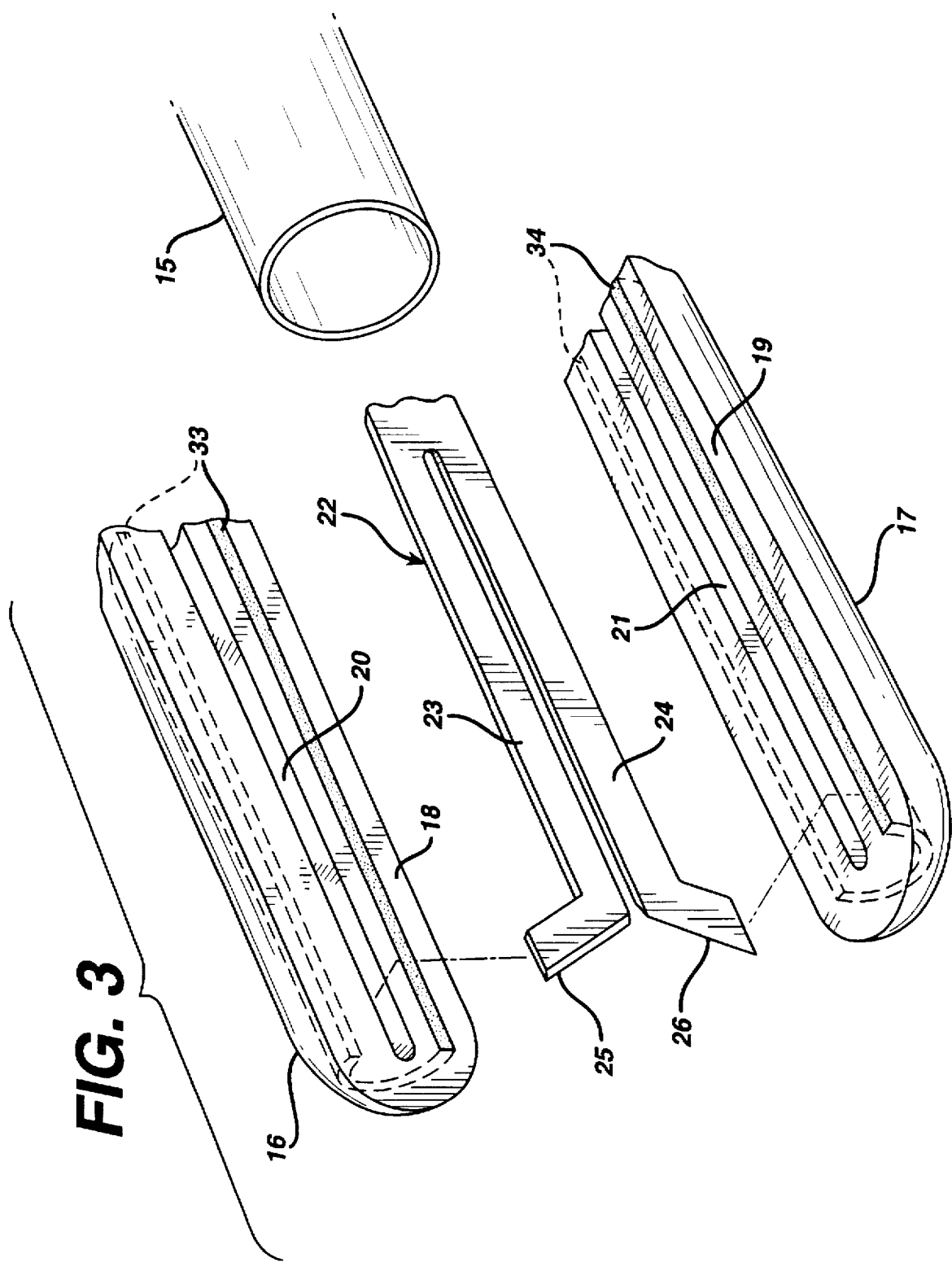
FIG. 3 is an exploded perspective view of the jaw members of the device illustrated in FIG. 1.

Referring now to FIGS. 1–7 there is illustrated a clamping and cutting instrument 10 of the present invention. The instrument 10 comprises a housing 11, a hollow sheath 12 extending distally from the housing 11, a jaw closure tube 15 comprised of an electrically insulative material extending through the sheath 12, and clamping jaw members 16, 17 extending from the distal end of closure tube 15. Jaw members 16 and 17 include opposed surfaces 18, 19 which are arranged to close towards each other to approximate tissue therebetween, upon advancing the closure tube 15 over camming surfaces 16a, 17a of jaw member 16, 17 respectively. Jaw members 16, 17 include grooves 20, 21 formed therein respectively, for receiving cutting element 22 as it is advanced through jaw members 16, 17. Cutting element 22 includes prongs 23, 24 separated at the distal end of the cutting element 22. The distal end of each prong 23, 24 is formed into a cutting blade 25, 26, respectively.

Blades 25, 26 are arranged to ride within grooves 20, 21 respectively as the cutting element 22 is advanced through jaw members 16, 17. Prongs 23, 24 overlap each other so that together the blades 25, 26 form a shearing or cutting member 50 for shearing tissue. Blades 25, 26 are angled so that when the prongs 23, 24 overlap the blades 25, 26 form a V-shaped shearing member. The prongs 23, 24 comprise a spring in which one or both of the prongs 23, 24 are biased away from each so that the blades 25, 26 will tend to separate from each other as the gap between jaw members 16, 17 increases, i.e., with thicker tissues. As the gap increases, the area of overlap decreases and the cutting member 50 size expands or increase as illustrated in FIG. 5. As the gap decreases the area of overlap increases and the cutting member 50 size contracts or decreases as illustrated in FIG. 4.

Jaw members 16, 17 include electrodes 33, 34, respectively, forming a portion of surface 18, 19 respectively. In this preferred embodiment the electrodes are offset from each other so that they will not contact each other if tissue is thin and/or will prevent arcing between electrodes. Electrode 33 is of a different electrical potential than electrode 34. A generator 35 provides electrosurgical energy to the electrodes 33, 34 and is activated by a user controlled footswitch 36. The generator 35 is preferably an electrosurgical unit capable of providing bipolar energy. The energy is delivered through wires 37 which are coupled through housing 11 to contacts 38, 39 associated with electrically isolated conductive portions 48, 49 of the closure tube 15.

A rotatable knob 28 extends from the housing 11. The knob engages sheath 12 and closure tube 15 which engages jaw members 16, 17. The knob 28 may be used to rotate the jaw members 16, 17 into position to grasp and clamp tissue.

After tissue is positioned between jaw members 16, 17 the jaw members 16, 17 are closed together to engage tissue between opposed surfaces of jaw members 16, 17. A pivoting handle member 30 is coupled to closure tube 15 and is arranged to rotate about pivot 41 to provide a translational longitudinal movement through linkage 40 to closure tube 15 over camming surface 16a, 17a, to close jaws together. Electrosurgical energy may then be supplied by activating footswitch 36.

After electrosurgical energy is applied and the tissue is electrosurgically treated to a desired degree, the cutting element 22 is advanced to cut the engaged tissue. The cutting element is actuated by pusher knob 31 which extends from outside housing 11 into closure tube 15 in housing 11. Pusher knob 31 is then coupled to drive rod 29 which extends through closure tube 15 and couples on its distal end to the cutting element 22. A spring 32 located in closure tube 15 abuts against the distal end of the pusher knob 31 and against the proximal end 27 of jaw members 16, 17. Spring 32 provides for the automatic retraction of the cutting element 22 when the pusher knob 31 is released.

Referring now to FIG. 8 there is illustrated an alternative embodiment of the present invention. Grooves 120, 121 in jaws 116, 117 include wavy or oscillatory surfaces 141, 142. As the cutting element 122 advances from proximally to distally, cutting blades 125, 126 of the cutting element 122 are in contact with surfaces 141, 142 which cause the blades 125, 126 to oscillate towards and away from each other with respect to a longitudinal axis 150. Thus, the surfaces 141, 142 provide an enhanced cutting effect, the nature of which depends on the size and shape of the waves (e.g. smaller waves with higher frequency provide more of a vibrating effect, longer waves provide more of a scissors like cutting effect.)

Referring now to FIG. 9 there is illustrated another alternative embodiment of the present invention. The sheath 212 defines a longitudinal axis extending proximally to distally along the instrument 210. The jaws 216, 217 curve about the axis to provide a curved end effector jaws for enhanced manipulation and visualization. A rotating knob 228 is coupled to the sheath 212. The cutting element 222 is frictionally engaged with the sheath 212. Thus, when the sheath 212 is rotated, so is the cutting element 212. This provides a fixed curve jaw which may be reoriented to appropriately grasp tissue.

Several variations of this invention have been described in connection with various surgical clamping and cutting instruments. Naturally, the invention may be used in numerous applications where clamping and cutting or clamping, cutting and coagulation is desired. Accordingly, it will be understood by those skilled in the art that various changes in modification may be made in the invention without departing from its scope which is defined by the following claims and their equivalents.

What is claimed is:

1. A surgical instrument comprising:

a shaft having a distal end; and an end effector located at the distal end of said shaft, said end effector comprising:

first and second elements comprised of first and second opposed tissue contacting surfaces respectively, said elements movable relative to each other from an open, spaced apart position for positioning tissue therebetween, to a closed position for approximating the tissue between the surfaces, said closed position defining a variable gap between said surfaces;

a cutting element comprising first and second cutting blades, said cutting element being movable with respect to said surfaces to divide tissue approximated between said surfaces;

wherein said end effector includes a mechanism to provide scissors-like cutting action between said blades as said cutting element is advanced;

said cutting element being adaptable in size to fit within said variable gap between said first and second surfaces.

2. The instrument of claim 1 wherein said end effector further comprises a proximal portion and a distal portion and a longitudinal axis extending proximally to distally through said end effector, and wherein said end effector includes a mechanism to cause oscillation of said cutting element about said longitudinal axis as said cutting element is advanced.

3. A surgical instrument comprising:

a shaft having a distal end;

an end effector located at the distal end of said shaft, said end effector comprising:

a cutting element;

first and second elements comprised of first and second opposed tissue contacting surfaces respectively, said elements movable relative to each other from an open, spaced apart position for positioning tissue therebetween, to a closed position for approximating the tissue between the surfaces, said closed position defining a variable gap between said surfaces, wherein at least one of said elements includes a groove therein, wherein said groove includes an oscillating surface;

said cutting element movable in said groove to divide tissue approximated between said surfaces, wherein said cutting element comprises one or more spring members biased in a cutting element expanding direction and wherein at least one of said spring members is biased towards said oscillating surface; and said cutting element being adaptable in size to fit within said variable gap between said first and second surfaces.

4. A surgical instrument comprising:

a shaft having a distal end;

an end effector located at the distal end of said shaft said end effector comprising:

first and second elements comprised of first and second opposed tissue contacting surfaces respectively, said elements movable relative to each other from an open, spaced apart position for positioning tissue therebetween, to a closed position for approving the tissue between the surfaces, said closed position defining a variable gap between said surfaces wherein each of said first and second elements includes a groove formed therein;

a cutting element movable in said groove to divide tissue approximated between said surfaces, wherein said cutting element comprises one or more spring members, each of said spring members including a blade formed at a distal end thereof and wherein one of said spring members is biased towards said first surface and one of said spring members is biased toward said second surface; and said cutting element being adaptable in size to fit within said variable gap between said first and second surfaces.

* * * * *